(12) United States Patent
Holmes et al.

(10) Patent No.: US 8,890,906 B2
(45) Date of Patent: Nov. 18, 2014

(54) METHOD AND SYSTEM FOR REMOTELY CALIBRATING DISPLAY OF IMAGE DATA

(75) Inventors: Colin John Holmes, Vancouver, WA (US); Pierre Joseph Lemire, Calgary (CA); Monroe Milas Thomas, Calgary (CA); Torin Arni Taerum, Calgary (CA)

(73) Assignee: Calgary Scientific Inc. (CA)

( * ) Notice: Subject to any disclaimer, the term of this patent is extended or adjusted under 35 U.S.C. 154(b) by 164 days.

(21) Appl. No.: 13/416,063

(22) Filed: Mar. 9, 2012

(65) Prior Publication Data

US 2012/0229526 A1 Sep. 13, 2012

Related U.S. Application Data

(60) Provisional application No. 61/487,610, filed on May 18, 2011.

(30) Foreign Application Priority Data

Mar. 11, 2011 (CA) ...................................... 2733860

(51) Int. Cl.
*G09G 5/10* (2006.01)
*G06F 3/14* (2006.01)

(52) U.S. Cl.
CPC .......... *G06F 3/14* (2013.01); *G09G 2320/0271* (2013.01); *G09G 5/10* (2013.01); *G09G 2340/14* (2013.01); *G09G 2370/022* (2013.01); *G09G 2320/0693* (2013.01); *G09G 2320/066* (2013.01); *G09G 2380/08* (2013.01); *G09G 2360/144* (2013.01)
USPC ....................................................... 345/690

(58) Field of Classification Search
CPC .............. G09G 2320/0233; G09G 2320/0626; G09G 2320/0693

USPC .......................................................... 345/690
See application file for complete search history.

(56) References Cited

U.S. PATENT DOCUMENTS 4,760,447 A 7/1988 Koka et al.
5,483,259 A 1/1996 Sachs
(Continued)

FOREIGN PATENT DOCUMENTS

EP 1662477 5/2006

OTHER PUBLICATIONS

"Canvys Releases CFS™ WebSuite Calibration Software for Image Systems Medical LCDs, Improving efficiency and productivity with web and mobile display calibration feedback system," Business Wire, Oct. 6, 2010, 2 pages.

(Continued)

*Primary Examiner* — Latanya Bibbins
(74) *Attorney, Agent, or Firm* — Meunier Carlin & Curfman, LLC

(57) ABSTRACT

A method for remotely calibrating display of image data is provided. Using a processor of the client computer display data are determined. The display data are indicative of a luminance dynamic range of the display and of an ambient lighting environment of the display. The display data are then transmitted to a server computer. Using a processor of the server computer display adjustment data are determined in dependence upon the display data. The display adjustment data are then transmitted to the client computer. Alternatively, image data for displaying on the display are received. Adjusted image data are then determined in dependence upon the received image data and the display adjustment data and transmitted to the client computer.

18 Claims, 5 Drawing Sheets

(56) References Cited

U.S. PATENT DOCUMENTS

| | | | |
|---|---|---|---|
| 5,883,985 A | 3/1999 | Pourjavid | |
| 5,910,792 A | 6/1999 | Hansen et al. | |
| 6,266,103 B1 | 7/2001 | Barton et al. | |
| 6,320,325 B1 | 11/2001 | Cok et al. | |
| 6,388,648 B1 * | 5/2002 | Clifton et al. | 345/88 |
| 6,633,657 B1 | 10/2003 | Kump et al. | |
| 6,927,784 B2 | 8/2005 | Matsuda et al. | |
| 7,106,285 B2 | 9/2006 | Naugler | |
| 7,190,411 B2 | 3/2007 | Cloutier | |
| 7,508,387 B2 | 3/2009 | Coley et al. | |
| 7,542,055 B2 | 6/2009 | Matsuda et al. | |
| 7,557,885 B2 | 7/2009 | Yamaguchi et al. | |
| 7,609,360 B2 | 10/2009 | Yamaguchi | |
| 7,907,135 B2 * | 3/2011 | Kuwabara et al. | 345/207 |
| 2003/0151781 A1 | 8/2003 | Ono | |
| 2006/0221025 A1 | 10/2006 | Breunig et al. | |
| 2007/0067124 A1 | 3/2007 | Kimpe et al. | |
| 2008/0049049 A1 | 2/2008 | Park et al. | |
| 2008/0094426 A1 | 4/2008 | Kimpe | |
| 2011/0012866 A1 * | 1/2011 | Keam | 345/175 |
| 2011/0254876 A1 * | 10/2011 | Yokoyama | 345/690 |
| 2012/0256943 A1 * | 10/2012 | Atkins et al. | 345/590 |

OTHER PUBLICATIONS

GE Healthcare, CT Clarity, "Taking Dose out of the Picture," 2009, 72 pages.

* cited by examiner

METHOD AND SYSTEM FOR REMOTELY CALIBRATING DISPLAY OF IMAGE DATA

CROSS-REFERENCE TO RELATED APPLICATION

The present application claims priority to U.S. Provisional Patent Application No. 61/487,610 filed May 18, 2011 and entitled "Method and System for Remotely Calibrating Display of Image Data," which is incorporated herein by reference in its entirety.

BACKGROUND OF THE DISCLOSURE

In many fields it is important that images displayed on electronic displays appear the same over time and on different displays. For example, in radiology it is important that a displayed medical image appears having the same contrast from year-to-year as a disease is followed or as the image is viewed on different displays. Therefore, standards exist for the calibration of displays to ensure consistency of display between devices and consistency over time. Color standards are often reached through International Color Consortium (ICC) related correction and calibration tools. In radiology, one industry standard for grayscale display and calibration is in Digital Imaging and Communications in Medicine (DI-COM) Part 14, the Gray Scale Display Function (GSDF), the content of which is incorporated herein by reference in its entirety.

It is common practice for medical device manufactures whose equipment contains or functions in association with a display system to offer GSDF or similar calibration as a product feature. This technology operates either as an integral unit to the device or as a third party add-on product. In the first case, a sensor within the display system monitors part or all of the luminance generated through the display's light path and supplies information to control components to correct or maintain the display response relevant to the GSDF. Medical physicists and other practitioners can monitor the changes in calibration requirements of various devices over time to ensure they are performing within limits and that the information displayed to physicians is displayed consistently.

Recently, there has been an increase in usage of client-server systems for the display of medical images. In this case, rather than images being generated on a designated medical device such as, for example, a PACS workstation or modality console with integral display components, the medical images are rendered on a central server and displayed on a client device which can be separated by a large distance from the server, and even outside the hospital where the server is deployed. Also, the client devices have evolved from closely controlled components of the medical device to commodity computers, laptops, tablet computers and even smart phones. The capacity of these devices to support internal or third party calibration varies widely.

While the designated medical devices have been used at fixed locations such as, for example, dark rooms or radiology reading rooms, the new devices are mobile and, therefore, introduce widely varying ambient light levels as a new variable to the calibration of image display. Mobile devices are used in widely varying situations such as, for example, offices, various other indoor locations (restaurants, theatres, residences) as well as outdoors, thus creating a wide range of possible lighting environments.

In addition to good manufacturing practice in industry, the application and routine maintenance of display quality assessments in the medical field can be a requirement for accreditation or reimbursement. With the adoption of mobile devices for these various color calibration or medical the Gray Scale Display Function (GSDF) consistency sensitive applications, the number of possible devices requiring monitoring may expand dramatically.

SUMMARY OF THE DISCLOSURE

The present disclosure provides methods and systems for remotely calibrating a display of image data. According to one aspect of the present disclosure, there is provided a method for remotely calibrating display of image data. Using a processor of the client computer display data are determined. The display data are indicative of a luminance dynamic range of the display and of an ambient lighting environment of the display. The display data are then transmitted to a server computer. Using a processor of the server computer display adjustment data are determined in dependence upon the display data. The display adjustment data are then transmitted to the client computer. Alternatively, image data for displaying on the display are received. Adjusted image data are then determined in dependence upon the received image data and the display adjustment data and transmitted to the client computer.

According to the aspect of the present disclosure, there is provided a method for remotely calibrating display of image data. The method includes receiving, at a server computer, a luminance dynamic range of a display of the computing device; receiving, at the server computer, an ambient lighting environment in which the display operates; determining display adjustment data in accordance with the luminance dynamic range and the ambient lighting environment; and if the display supports calibration, providing the display adjustment data to the computing device to adjust the image data, or if the display does not support calibration, communicating adjusted image data to the computing device.

According to another aspect of the present disclosure, there is provided an apparatus for remotely calibrating a display of image data. The apparatus includes a network interface; a memory that stores computer executable instructions; and a processor that executes the computer executable instructions. The instructions cause the apparatus to receive display data from a client computer indicative of a luminance dynamic range of a display of the computing device and an ambient lighting environment in which the display operates; determine display adjustment data in accordance with the luminance dynamic range and the ambient lighting environment of the computing device; and if the display supports calibration provide the display adjustment data to the computing device to adjust the image data, or if the display does not support calibration, communicate adjusted image data to the computing device.

According to another aspect of the present disclosure, there is provided a method for remotely calibrating display of image data on a computing device. The method includes determining a luminance dynamic range of a display of the computing device; determining an ambient lighting environment in which the display operates; communicating the luminance dynamic range and the ambient lighting environment to a server computer that determines display adjustment data in accordance with the luminance dynamic range and the ambient lighting environment; and if the display supports calibration, receiving the display adjustment data to adjust the image data, or if the display does not support calibration, receiving adjusted image data.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAIL DESCRIPTION OF THE DISCLOSURE

Unless defined otherwise, all technical and scientific terms used herein have the same meaning as commonly understood by one of ordinary skill in the art. While implementations of the disclosure will be described for remotely calibrating image data on certain devices, it will become evident to those skilled in the art that the implementations of the disclosure are not limited thereto, but are applicable for remotely calibrating image data for display on any type of computing device.

Figure 1:
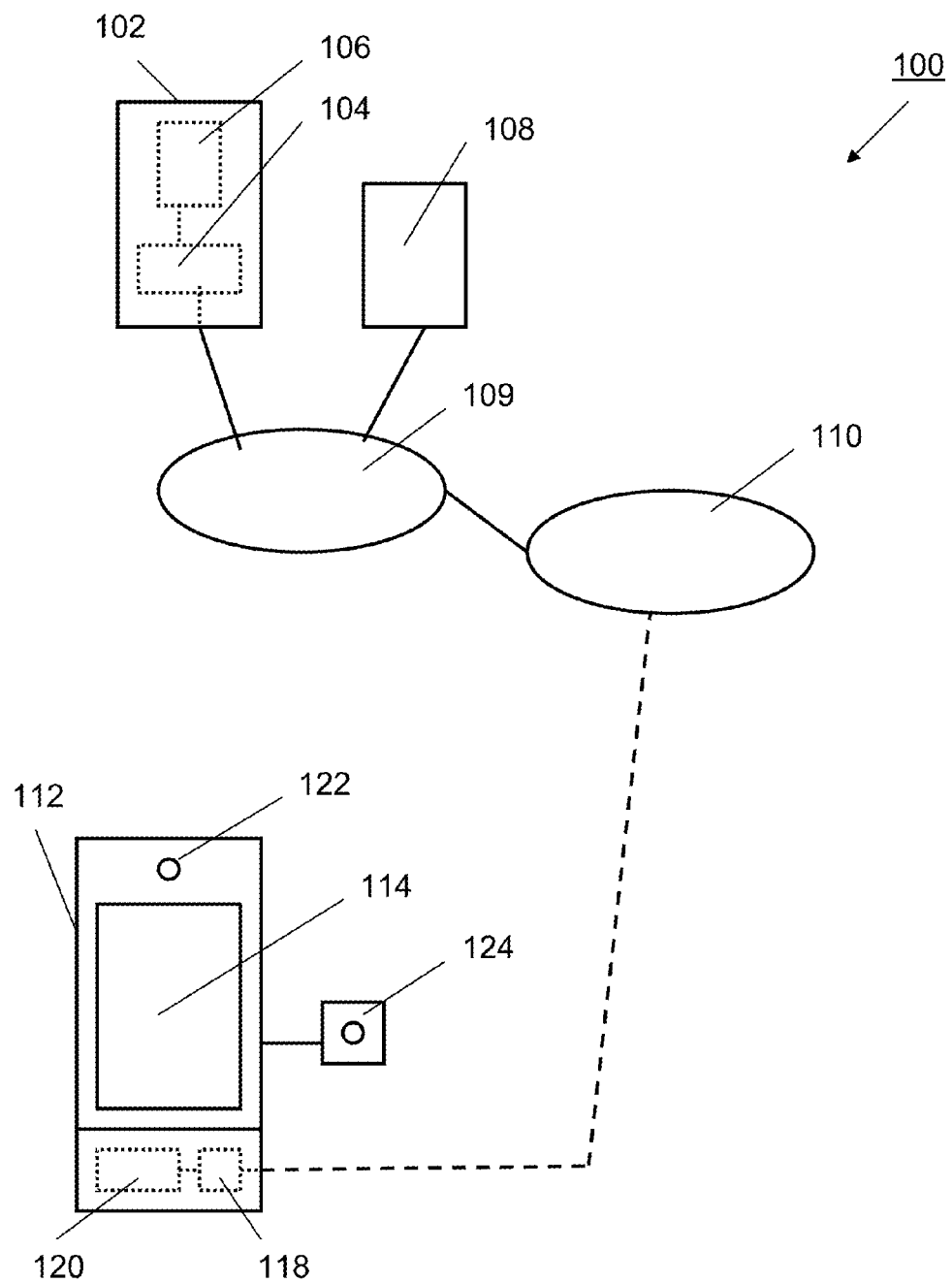
FIG. 1 is a simplified block diagram illustrating a system for remotely calibrating display of image data according to a implementation of the disclosure.

Referring to FIG. 1, there is illustrated a system 100 for providing remote calibration via, e.g., a computer network according to an implementation of the disclosure. The system comprises a client computer 112, e.g., a wireless handheld device such as an IPHONE or a BLACKBERRY connected via a computer network 110 such as, for example, the Internet, to server computer 102. The server computer 102 may be part of a Local Area Network (LAN) 109, for example, the LAN of a hospital. The client computer 112 may be any computing device, e.g., a tablet device, a desktop computer, a workstation, a notebook computer, etc., having a suitable display to render image or video data in accordance with the below.

Remote calibration of a display associated with the client computer 112 may be performed by executing executable commands of a client calibration program stored in memory 120 using processor 118 of the client computer 112. For example, the client calibration program may determine display data indicative of a luminance dynamic range of the display 114 and of an ambient lighting environment in which the display 114 operates. The display data are then transmitted via the computer networks 110 and 109 to the server computer 102.

In accordance with the display data, executable commands of a server calibration program stored in memory 106 are executed using processor 104 of the server computer 102 to determine display adjustment data. If the display 114 supports calibration, the processor 104 retrieves the image data for display from database 108 and provides the same together with the display adjustment data to the processor 118 of the client computer 112. The image data for display may be adjusted by the client computer 112. On the other hand, if the display 114 does not support calibration, the processor 104 retrieves the image data for display from database 108, determines adjusted image data in dependence upon the image data and the display adjustment data, and transmits the adjusted image data to the processor 118 of the client computer 112. Upon receipt, the processor 118 of the client computer 112 controls the display 114 in accordance the display adjustment data and provides the image data for display, or provides the adjusted image data for display. Alternatively, the server calibration program is executed on a processor of a second server computer connected to the server computer 102 and the client computer 112 via the computer network 110. Optionally, provision of a client calibration program is omitted and the display data are provided, for example, as user input data via a suitable web browser.

Figure 2:
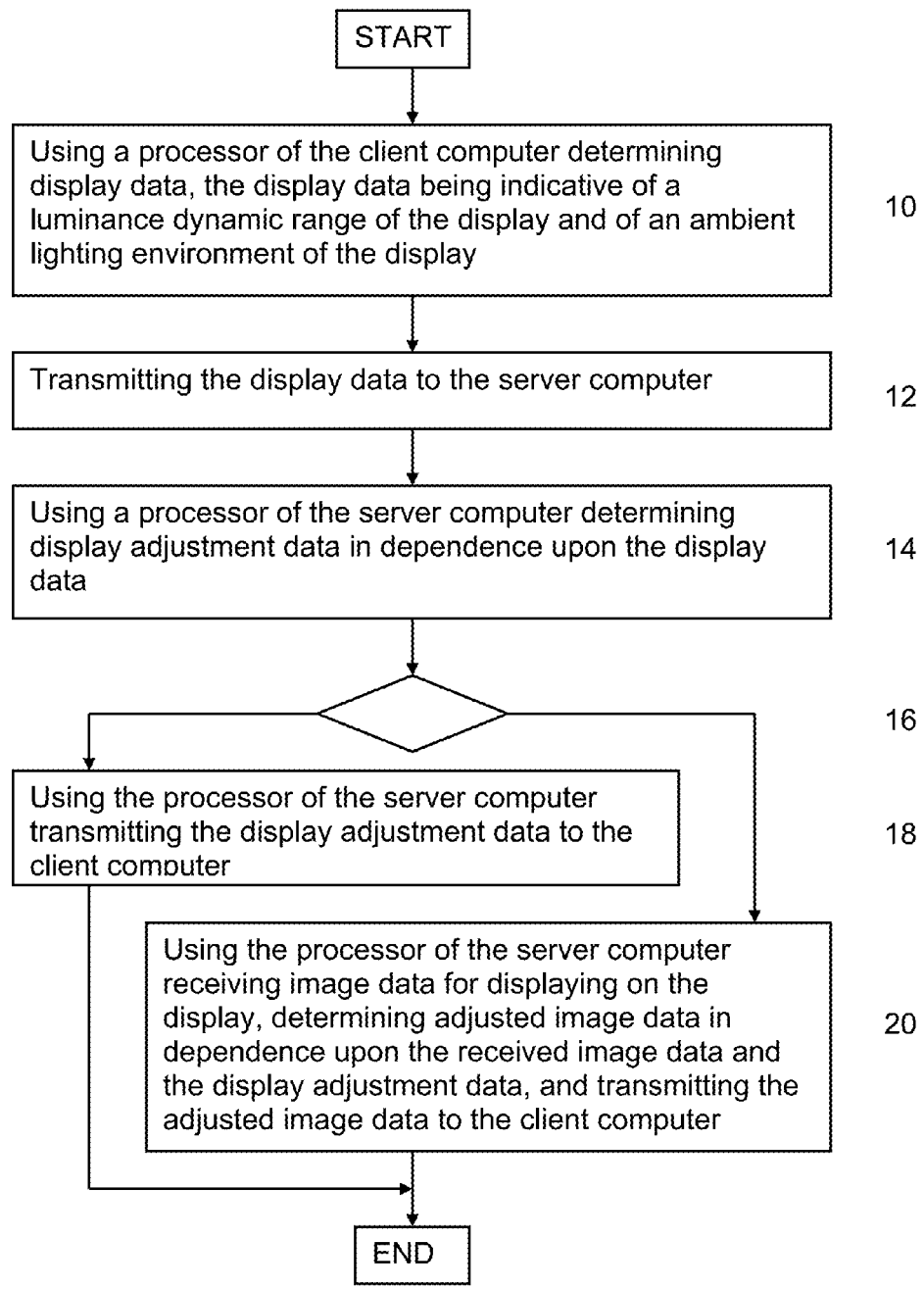
FIG. 2 is a simplified flow diagram illustrating a method for remotely calibrating display of image data according to a implementation of the disclosure.

Referring to FIG. 2, there is illustrated a flow diagram of a method for remotely calibrating display of image data according to an implementation of the present disclosure. At 10, display data are determined using processor 118 of the client computer 112. The display data are indicative of a luminance dynamic range of the display and of an ambient lighting environment of the display. Data indicative of the luminance dynamic range of the display may be, for example, provided by the manufacturer of the display and retrievably stored in memory 120 of the client computer 112.

Alternatively, data indicative of a plurality of dynamic luminance dynamic ranges such as, for example, 8-bit range (255 pixel values) or 10-bit range (1024 pixel values) and their association to respective types of displays may be stored in the form of a look-up table in the memory 106 of the server computer 102. Upon receipt of data indicative of the type of display, for example, provided by the user or retrieved from the memory 120 of the client computer 112, the processor may retrieve the respective luminance dynamic range using the look-up table. Further alternatively, the data indicative of the luminance dynamic range may be obtained using an external photometer 124. In accordance with such an aspect of the disclosure, the minimum illumination may first be measured by filling the display 114 with the lowest intensity pixel value and measuring the minimum output luminance of the display. Next, the maximum illumination is measured by filling the display 114 with the highest intensity pixel value and measuring the maximum output luminance of the display. The luminance dynamic range may then be determined as the difference between the maximum output luminance and the minimum output luminance. The above may be performed, for example, once before using the display and the data are stored in memory 120 of the client computer 112. Optionally, the measurement is repeated in predetermined intervals to update the luminance dynamic range of the display 114 to take, for example, aging effects of the display 114 into account.

Figure 3A:
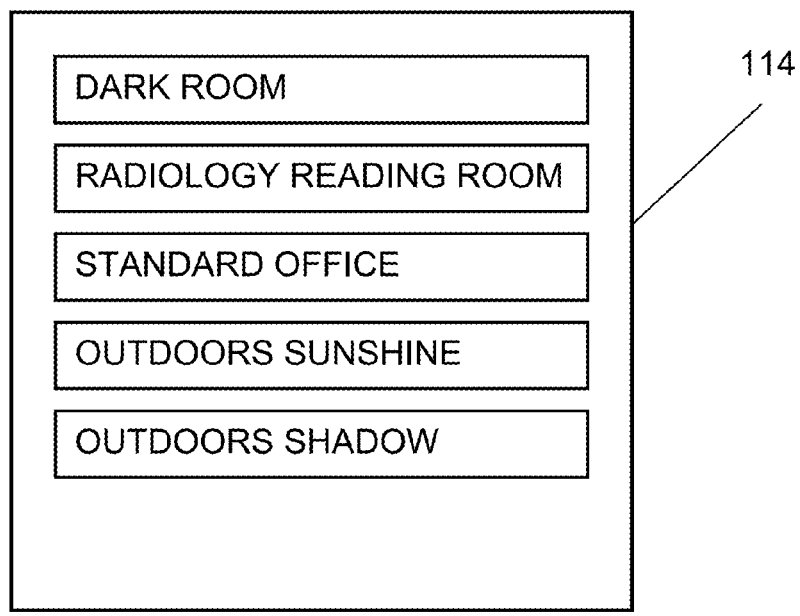
FIG. 3a is a simplified block diagram illustrating a screen for determining ambient lighting of the display in the method illustrated in FIG. 2.

To determine the data indicative of the ambient lighting environment in which the display 114 operates, the user of the client computer 112 may be, for example, provided with a list of representative lighting environments, as illustrated in FIG. 3a. Representative ambient lighting environments are, for example, a dark room or minimum lighting (approx. 30 lux), a radiology reading room (approx. 100 lux), a standard office lighting (approx. 300 lux), and outdoors (approx. 450 lux). Alternatively, the ambient lighting may be measured using a photometer integral to the client computer 112 such as, for example, built-in camera 122 or an external photometer connected to the client computer 112.

At 12, data indicative of the measured ambient lighting is processed and transmitted together with the data indicative of the luminance dynamic range of the display 114 to the server computer 102. At 14, after receipt of the display data at the server computer 102, display adjustment data are determined using the processor 104 of the server computer 102. For example, as a first step, a lowest and a highest Just Noticeable Difference (JND) are determined as follows:

$$JND_{min}=JND(Luminance_{min}+Ambient\ Lighting)$$

$$JND_{max}=JND(Luminance_{max}+Ambient\ Lighting)$$

followed by the determination of the perceptual dynamic range:

$$JND_{perc}=JND_{max}-JND_{min},$$

where the JND is the luminance difference of a given target under given viewing conditions that the average human observer can just perceive.

Display adjustment data may then be determined such that the adjusted luminance dynamic range of the display 114 substantially matches the perceptual dynamic range. For example, the Gray Scale Display Function (GSDF) function is employed to determine the pixel values that will step the display one JND at a time in a nonlinear fashion using the remaining luminosity capability of the display 114. Alternatively, the pixel values are determined using other functions or a look-up table.

Figure 3B:
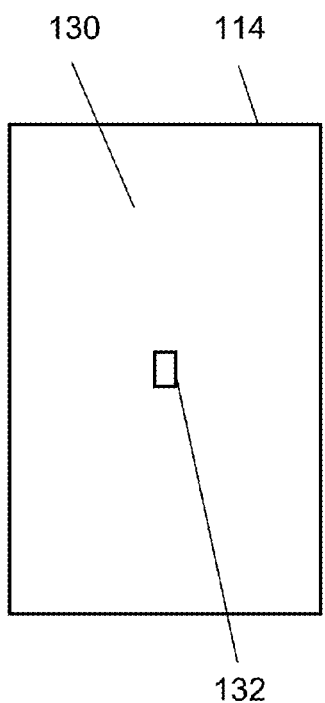
FIGS. 3b and 3c are simplified block diagrams illustrating contrast images for determining display data in the method illustrated in FIG. 2.
Figure 3C:
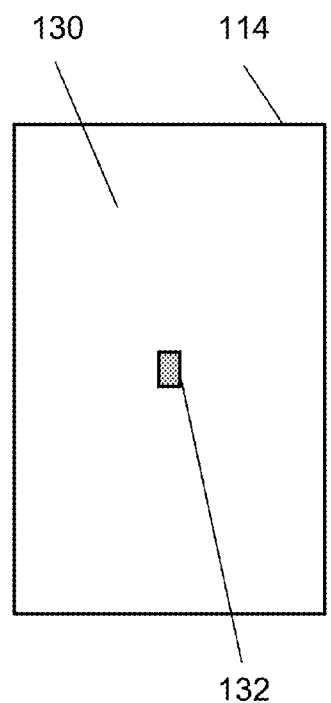

Alternatively, the perceptual dynamic range may be determined by the user. For example, a user of the display 114 may be presented with a first series of contrast images. Two exemplary contrast images are illustrated in FIGS. 3b and 3c. As shown, each contrast image comprises a target 132 and a surround 130, with the surround having pixels values determined, for example, by common practice or as specified in applicable standard (e.g., VESA Flat Panel Display Measurement, ACR Task Group 18, DICOM Part 14, SMPTE). In the first series, the target pixel values increase with each subsequent image. The user then identifies the contrast image in which the target 132 is first distinguishable from the surround 130. The difference of the target and surround pixel values of the indentified image is associated with the $JND_{min}$. Next, the user may be presented with a second series of contrast images. Each contrast image in the second series of images comprises a target 132 and a surround 130 with the surround having high-valued pixels determined, for example, by common practice or as specified in an applicable standard. In the second series, the target pixel values decrease with each subsequent image. The user identifies the contrast image in the second series in which the target 132 is first distinguishable from the surround 130. The difference of the target and surround pixel values of the indentified image is associated with the $JND_{max}$.

In accordance with implementations of the present disclosure, the target 132 comprises, for example, one block of pixels placed approximately in the center of the display 114. Alternatively, the target 132 comprises a plurality of pixels forming a predetermined shape such as, for example, a circle, a rectangle, a cross, etc. Alternatively, the target 132 is displaced to a random location on the screen or comprises a group of targets as determined by common practice or as specified in applicable standards.

Optionally or additionally, the ambient lighting may be measured when the user identifies $JND_{min}$ and $JND_{max}$. An association of the $JND_{min}$ and $JND_{max}$ with the ambient lighting may be created. The $JND_{min}$ and $JND_{max}$ and the associated ambient lighting data may then stored in memory 120 of the client computer, for example, in the form of a look-up table. During use of the client computer 112, if an ambient lighting is measured which is within a predetermined range of the stored ambient lighting, a determination of the $JND_{min}$ and $JND_{max}$ by the user may be omitted. In this instance, the respective data may be retrieved from the memory 120 and provided to the server computer 102.

At 16, if the display 114 supports calibration, then at 18, processor 104 retrieves the image data for display from the database 108 and provides the same together with the display adjustment data to the processor 118 of the client computer 112. Optionally, the processor 104 may provide only the display adjustment data, while the image data are provided from another location. Upon receipt, the processor 118 of the client computer 112 controls the display 114 in dependence upon the display adjustment data and provides the image data for display, or provides the adjusted image data for display. If, at 16, the display 114 does not support calibration, then at 20, the processor 104 retrieves the image data for display from database 108, determines adjusted image data in accordance with the image data and the display adjustment data, and transmits the adjusted image data to the processor 118 of the client computer 112.

With regard to the flow diagram of FIG. 2, an alternative to sending the luminance changes to the client computer is to perform the changes on the image on the server computer and send the altered image (requiring no further modification) to the client computer for display. Such an implementation may be used for devices that are not capable of altering the display look up table in use.

Further optionally, the display adjustment data may be used for display of video data. For example, the display adjustment data are transmitted once before display of a sequence of image frames of the video data or an adjusted image frame is determined for each image frame of the video data using the display adjustment data.

Yet further, in some implementations, the ambient lighting may be measured during display of the image data, for example, in predetermined time intervals and when a change in the ambient lighting is detected data indicative of the new ambient lighting are provided to the server computer 102, which then updates the display adjustment data for adjusting the display of the image to the changed ambient lighting. Updating of the data indicative of the ambient lighting is useful during display of an image for a longer time interval, when a user changes his/her location, or during display of video data. For example, during display of video data the display adjustment data are changed for the display of subsequent image frames of the video if a change of the ambient lighting is detected. The server computer 102 then provides updated display adjustment data to the client computer 112 or determines the adjusted image frames of the video using the updated display adjustment data.

Further optionally, data indicative of the luminance dynamic range of the image to be displayed are determined in dependence upon the display adjustment data and provided for display to the user. This feature provides the user with a quantitative assessment of the luminance dynamic range of the image. Further optionally, the user is provided with an indication if predetermined standards are not met by the current display of the image.

Figure 4:
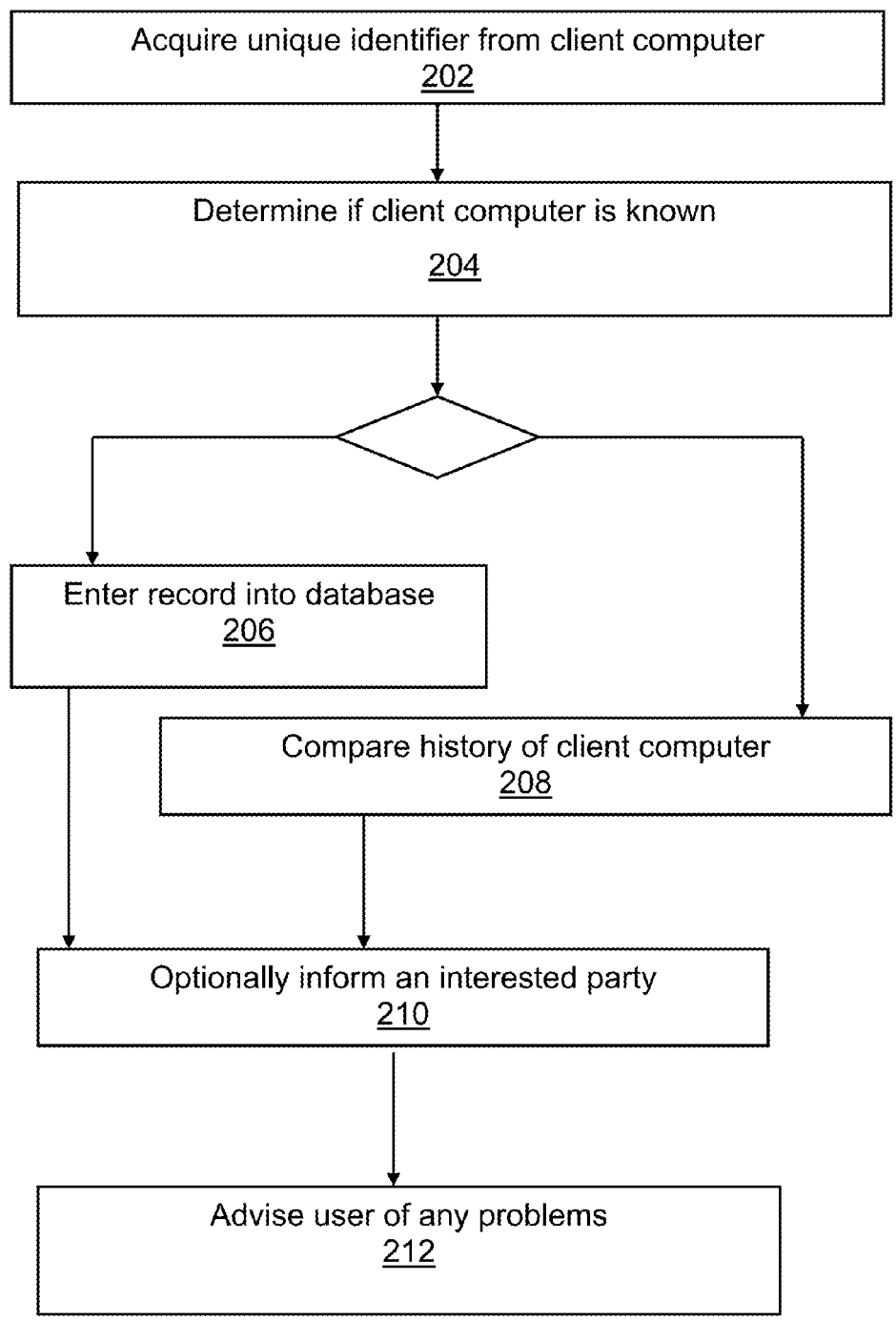
FIG. 4 illustrates a flow diagram of processes performed to identify and track a client computer within the system of FIG. 1.

In accordance with some implementations, FIG. 4 illustrates a flow diagram of processes performed to identify and track the client computer. For example, the tracking and identification may implement to maintain consistency of the display characteristics across client computers 112 accessing a particular server computer 112. The tracking may also identify a client computer 112 that is out-of-specification and in need of attention/repair.

At 202, using a client software connection, a device specific unique identifier may be acquired from the client computer. For example, a MAC address of the device's communications components may be acquired or some another unique identifier (e.g., a GUID) maintained by the client computer 112. This information may be transmitted with the display data (as described with reference to FIG. 2) or separately. At 204, it is determined if the client computer is known. If not, then at 206 a record may be entered into a database. The database may be maintained by or on behalf of the sever computer 102 to track the client computers. If the client computer is known, then at 208, the current state of the computer as conveyed in the display data is compared to the previous history of the client computer. At 210, information regarding the new client computer or the known client computer may be optionally communicated to an interested party. For example, quality assurance staff may wish to be informed when/if client computers are accessing the server computer 102. At 212, a user is advised if the client computer is out of calibration or out of specification such that appropriate action may be taken. For example, if the client computer may need repair or may provide inaccurate image production, the user may be advised in order to prevent, e.g., an incorrect diagnosis.

Thus, in the above, the method for remotely calibrating display of image data may be implemented using standard programming technologies and standard digital encoding formats for processing the image/video data. Software for the central server system is programmed using, for example, the Microsoft Visual Studio development environment. Client devices are programmed using native application programming interfaces and software in languages appropriate to each device, for example, Objective C, C# and Java.

The present disclosure has been described herein with regard to implementations. However, it will be obvious to persons skilled in the art that a number of variations and modifications can be made without departing from the scope of the disclosure as described herein.

What is claimed is:

1. A method for remotely calibrating display of image data on a computing device, comprising:
receiving, at a server computer, a luminance dynamic range of a display of the computing device;
receiving, at the server computer, an ambient lighting environment in which the display operates;
determining display adjustment data in accordance with the luminance dynamic range and the ambient lighting environment, the display adjustment data being further determined using a lowest Just Noticeable Difference (JND) and a highest JND as follows:

$$JND_{min}=JND(Luminance_{min}+Ambient\ Lighting)$$

$$JND_{max}=JND(Luminance_{max}+Ambient\ Lighting);\ and$$

determining a perceptual dynamic range as $JND_{perc}=JND_{max}-JND_{min}$; and
if the display supports calibration, providing the display adjustment data to the computing device to adjust the image data, or if the display does not support calibration, communicating adjusted image data to the computing device.

2. The method of claim 1, further comprising storing the display adjustment data in a memory of the computing device.

3. The method of claim 1, further comprising:
storing a plurality of luminance dynamic ranges in a lookup table;
associating the plurality of luminance dynamic ranges with respective display types; and
retrieving display data in the lookup table.

4. The method of claim 1, further comprising obtaining the luminance dynamic range using an external photometer.

5. The method of claim 4, further comprising:
determining a minimum illumination of the display of the computing device by filling the display with a lowest intensity pixel value;
measuring a minimum output luminance of the display;
determining a maximum illumination of the display by filling the display with a highest intensity pixel value;
measuring a maximum output luminance of the display; and
determining the luminance dynamic range based on a difference between the maximum output luminance and the minimum output luminance.

6. The method of claim 1, further comprising determining data indicative of the ambient lighting environment of the display in accordance with a selection of a predetermined type of ambient lighting environment.

7. The method of claim 1, determining luminance dynamic range further comprising:
presenting a series of contrast images having a target area and a surround area, the target area and the surround area having respective predetermined target pixel values that are increased for each subsequent contrast image presented;
receiving an identification of a contrast image wherein the target area is distinguishable from the surround area and associating an identified contrast image as $JND_{min}$;
presenting a second series of contrast images having a target area and a surround area, the target area and the surround area having respective predetermined target pixel values that are decreased for each subsequent contrast image presented; and
receiving an identification of a second contrast image wherein the target area is distinguishable from the surround area and associating an identified second contrast image as $JND_{max}$.

8. The method of claim 1, further comprising:
measuring the ambient lighting; and
associating $JND_{min}$ and $JND_{max}$ with the measure ambient lighting.

9. The method of claim 1, wherein the image data comprises video data.

10. An apparatus for remotely calibrating a display of image data, comprising:
a network interface;
a memory that stores computer executable instructions; and
a processor that executes the computer executable instructions to:
receive display data from a client computer indicative of a luminance dynamic range of a display of a computing device and an ambient lighting environment in which the display operates;
determine display adjustment data in accordance with the luminance dynamic range and the ambient lighting environment of the computing device, the display adjustment data being further determined using a lowest Just Noticeable Difference (JND) and a highest JND as follows:

$$JND_{min}=JND(Luminance_{min}+Ambient\ Lighting)$$

$$JND_{max}=JND(Luminance_{max}+Ambient\ Lighting);\ and$$

determining a perceptual dynamic range as $JND_{perc}=JND_{max}-JND_{min}$; and if the display supports calibration provide the display adjustment data to the computing device to adjust the image data, or if the display does not support calibration, communicate adjusted image data to the computing device.

11. The apparatus of claim 10, the processor further executing instructions to:
store a plurality of luminance dynamic ranges in a lookup table;
associate the plurality of luminance dynamic ranges with respective display types; and
retrieve display data in the lookup table.

12. The apparatus of claim 10, wherein the adjustment data is determined such that an adjusted luminance dynamic range of the display substantially matches the perceptual dynamic range.

13. The apparatus of claim 10, wherein the image data comprises video data.

14. The apparatus of claim 10, the processor further executing instructions to track the computing device and to maintain a history of the computing device.

15. A method for remotely calibrating display of image data on a computing device, comprising:
determining a luminance dynamic range of a display of the computing device;
determining an ambient lighting environment in which the display operates;
communicating the luminance dynamic range and the ambient lighting environment to a server computer that determines display adjustment data in accordance with the luminance dynamic range and the ambient lighting environment, the display adjustment data being further determined using a lowest Just Noticeable Difference (JND) and a highest JND as follows:

$JND_{min}=JND(Luminance_{min}+Ambient\ Lighting)$ $JND_{max}=JND(Luminance_{max}+Ambient\ Lighting)$; and determining a perceptual dynamic range as $JND_{perc}=JND_{max}-JND_{min}$; and if the display supports calibration, receiving the display adjustment data to adjust the image data, or if the display does not support calibration, receiving adjusted image data.

16. The method of claim 15, further comprising storing the display data in a memory of the computing device.

17. The method of claim 15, further comprising determining data indicative of the ambient lighting environment of the display in accordance with a selection of a predetermined type of ambient lighting environment.

18. The method of claim 15, determining luminance dynamic range in accordance with a Just Noticeable Difference (JND), the method further comprising:
presenting a series of contrast images having a target area and a surround area, the target area and the surround area having respective predetermined target pixel values that are increased for each subsequent contrast image presented;
receiving an identification of a contrast image wherein the target area is distinguishable from the surround area and associating an identified contrast image as $JND_{min}$;
presenting a second series of contrast images having a target area and a surround area, the target area and the surround area having respective predetermined target pixel values that are decreased for each subsequent contrast image presented; and
receiving an identification of a second contrast image wherein the target area is distinguishable from the surround area and associating an identified second contrast image as $JND_{max}$.

* * * * *